United States Patent [19]
Vecchi

[11] Patent Number: 5,391,738
[45] Date of Patent: Feb. 21, 1995

[54] PROCESS FOR THE SEPARATION OF FOLINIC ACIDS

[75] Inventor: Guiseppe Vecchi, Aldesago, Switzerland

[73] Assignee: APR Applied Pharma Reserach S.A., Stabio, Switzerland

[21] Appl. No.: 104,129

[22] PCT Filed: Jan. 20, 1993

[86] PCT No.: PCT/EP93/00127

§ 371 Date: Aug. 16, 1993

§ 102(e) Date: Aug. 16, 1993

[87] PCT Pub. No.: WO93/15076

PCT Pub. Date: Aug. 5, 1993

[30] Foreign Application Priority Data

Jan. 22, 1992 [CH] Switzerland .................. 00175/92

[51] Int. Cl.$^6$ ............................ C07D 475/04
[52] U.S. Cl. ................................ 544/258
[58] Field of Search ........................ 544/258

[56] References Cited

U.S. PATENT DOCUMENTS

| 4,959,472 | 9/1990 | Wood et al. | 544/258 |
| 5,006,655 | 4/1991 | Mueller et al. | 544/258 |
| 5,010,194 | 4/1991 | Mueller et al. | 544/258 |
| 5,134,235 | 7/1992 | Mueller et al. | 544/258 |
| 5,194,611 | 3/1993 | Marazza et al. | 544/258 |
| 5,324,836 | 6/1994 | Mueller et al. | 544/258 |

FOREIGN PATENT DOCUMENTS

| 266042 | 5/1988 | European Pat. Off. | 544/258 |
| 348641 | 1/1990 | European Pat. Off. | |
| 356934 | 3/1990 | European Pat. Off. | |
| 367902 | 5/1990 | European Pat. Off. | |
| 432441 | 6/1991 | European Pat. Off. | |
| 0455013 | 11/1991 | European Pat. Off. | 544/258 |
| 0495204 | 7/1992 | European Pat. Off. | |
| 0537842 | 4/1993 | European Pat. Off. | 544/258 |
| 88-08844 | 11/1988 | WIPO | |
| 91-13890 | 9/1991 | WIPO | |

OTHER PUBLICATIONS

Aitilio et al Chemical Abstr. vol 120, Entry 288693 (1993) abstracting EP 539987.

Vecchi Chemical Abstr. vol. 119 Entry 270915 (1993) abstracting EP 537,842.

*Primary Examiner*—Donald G. Daus
*Attorney, Agent, or Firm*—Nixon & Vanderhye

[57] ABSTRACT

The treatment of racemic calcium folinate with a sodium salt of ethylendiaminotetraacetic acid and, preferably, calcium cloride determines the separation of a precipitate, whose mother liquors result enriched in a calcium salt of the levofolinic acid, purifiable through repeated crystallizations.

5 Claims, No Drawings

PROCESS FOR THE SEPARATION OF FOLINIC ACIDS

The present invention relates to a process for the separation of folinic acids and for the obtention of the (6S(−)) diastereoisomer, particularly as the calcium salt. The separation of the mixture of diastereoisomers consisting of the [6(R,S)-$N^5$-formyltetrahydrofolic] acid has a great interest since only the (6S) diastereoisomer (levofolinic acid) is endowed with biological and pharmacological activity. The form in which the folinic acid is mostly administered is that of the calcium salt thereof.

Thus a process for the isolation of the levofolinic acid directly as the calcium salt has a great industrial importance.

To this end a research work has been started in order to evaluate the possibility of sequestering part of the calcium ion released from an aqueous solution of racemic calcium folinate, in the presence of a suitable chelating agent such as the sodium salt of the ethylendiaminotetraacetic acid (tetrasodium EDTA), The purpose was that of achieving the relative precipitation of the calcium S-(−)-folinate, described as the less soluble of the two diastereoisomers (Lederle patent PCT/EP 88/00341), keeping the other diastereoisomer in form of sodium salt.

It has been surprisingly found and is the object of the present invention that, by treating a solution of racemic calcium folinate with tetrasodium EDTA in the ratio of half mole thereof per mole of folinate and salting out the solution with sodium chloride, in order to promote the precipitation of the less soluble species, the mother liquors, upon being separated from the thus obtained precipitate, are highly enriched with the less soluble species, namely calcium S-(−)-folinate, which can be obtained at the solid state by adding calcium chloride and filtering the precipitate.

A more extended investigation has been carried out about the causes of such a surprising behaviour. The optimization tests, aiming to increase yield and optical purity of the precipitate enriched with the levorotatory form, have casted some light on the probable mechanism involved.

It has been firstly found that the best yields are obtained by adding to the starting solution, besides the half mole of tertasodium EDTA, half mole of calcium chloride; however, in order to precipitate the enriched levorotatory form from the mother liquors it is necessary to add the filtrate with a further half mole of calcium chloride. The weight ratios between the first precipitate, obtained after the salting out, and the second one, enriched with the levorotatory form, together with the determination of the folinic acid in the two precipitates by means of HPLC, lead to the conclusion that the first precipitate essentially consists of a mixture of calcium edetate and calcium folinate, whereas the second precipitate does not contain great amounts of EDTA.

A hypothesis consistent with these data, although herein reported without limiting intention, is that a mixed salt is formed in solution, which can be represented by the structure (1), it being more insoluble either than calcium folinate and than EDTA salts. Moreover of the two forms which can be originated, it is to be supposed that the one formed by EDTA and calcium d-folinate is the most insoluble.

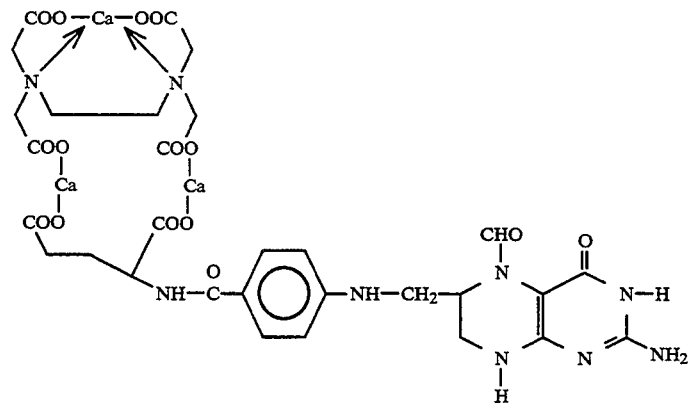

(1)

Another evidence confirming such a supposition is the fact that if an attempt is made of forcing the first precipitation by cooling the solution after the salting out, the result is poor, contrarily to what could have to be expected if it would be a mere precipitation of an insoluble species already present in the starting solution. This phenomenon can be on the contrary adequately interpreted by making the supposition that an insoluble species (mixed salt) is formed in the solution according to the times dictated by the reaction kinetics.

It has been found that, as a matter of fact, the maximum amount of precipitate after the salting out is obtained by heating the mixture or by increasing the stirring times.

The optimization of the operating conditions leads to a significant result from the point of view of the preparation of calcium S-(−)-folinate. The second precipitate, as obtained by treating with calcium chloride the mother liquors of the first one, as a matter of fact has a weight on dry basis which is slightly higher than half of the weight of racemic calcium folinate used as the starting compound. It consists of about 70% of calcium folinate. The polarimetric analysis reveals that the latter is divided in the diastereoisomer R-(+) by about 25% and in the S-(−) diastereoisomer by the remaining 75%. It is to be noticed that like percentages, although inverted with respect to the two diastereoisomers are found in the first precipitate, containing most of the EDTA probably in form of mixed salt (1).

The thus achieved enrichment can be exploited to obtain the S-(−) diastereoisomer in pure form. The necessary process consists in repeated crystallizations of the product enriched in the S-(−) form.

These operations simultaneously fulfill two functions: to remove the EDTA possibly present in the product and to subsequently enrich the diastereoisomer already present in the 75% content to bring it to the desired concentration.

Both functions are fulfilled by the crystallization of the product of first enrichment in aqueous solution, made alkaline enough by adding ammonia.

The alkalinity is necessary both to make the EDTA free from the fraction of mixed salt of type (1) remaining in the enriched product, and to depress the solubility of the calcium folinate. As a matter of fact, it is known that at neutral pH the nitrogen atoms of the pteridinic moiety of the calcium folinate are partially protonated thus showing the behaviour of the strong bases, and that the addition of alkali causes the precipitation of the calcium folinate itself.

The following example discloses for merely illustrative purpose the present invention.

EXAMPLE

In a 1 liter flask having a mechanical stirrer 450 ml of distilled water and 100 g of racemic calcium folinate are charged. By stirring at room temperature the product is almost immediately solubilized. Then 31 g of disodium EDTA and 6.67 g of soda flakes are charged in a quick succession, and the stirring is continued for half a hour. The thus obtained solution is added with 10 g of anhydrous calcium chloride. The mixture is maintained under stirring for half a hour. Then 120 g of sodium chloride are added. As the sodium chloride is dissolved a yellow microcristalline solid is quickly precipitated. The suspension is stirred for two hours. Meanwhile the precipitate increases whereby the suspension is converted into a stirrable paste. The latter is diluted with further 150 ml of distilled water. The stirring is continued for one hour further. The suspension is filtered under vacuum. The precipitate is squeezed for a long time, but not washed, so as to recover quite exactly 600 ml of yellow solution. The latter is poured in a 1 liter becker and treated under stirring with 10 g of anhydrous calcium chloride. The thus formed suspension is stirred for half a hour at room temperature and then filtered under vacuum.

The precipitate can be isolated in a dry form, for the analysis, by dispersing in anhydrous ethanol, filtration and drying at 60° C. The thus obtained dry product has a content of calcium folinate as assessed by HPLC of about 70% referred to the dry product, whereas the polarimetric analysis shows a specific rotatory optical power, corrected according to the HPLC titration, ranging between 0 and +1.5°.

The product, even in the non dried condition, undergoes repeated crystallizations according to the hereinafter reported proceeding: the product is suspended in a volume of distilled water equal to 8 to 10 times the dry weight thereof. If necessary, the pH is corrected to 5.5 with concentrated hydrochloric acid. The temperature is brought to 55°-60° C. Either calcium or sodium cloride at a quarter of the weight on dry basis of the product is added. Always at 55°-60° C, the pH is adjusted to 9.2 by means of ammonia. The solution is then left to crystallize without stirring, firstly at room temperature for two hours and then, at 2°-4° C. for one night. The product is filtered under vacuum.

Typical results are the following: after the first crystallization the HPLC titer, as determined according to the analytical specifications provided by USP XXI for calcium folinate, is found to be of between 90 and 95%, whereas the specific rotatory optical power, corrected according to the concentration, has a value ranging between −5° and −2°. After the third crystallization the optical power decreases to values oscillating between −12° and −15°, whereas the HPLC titer is found to be higher than 98%.

The product which has achieved the desired characteristics, after filtration under vacuum, is slurried in 95% ethanol. During this operation the pH is corrected with a small amount of concentrated HCl until values of between 6.5 and 7 are obtained. The product is lastly filtered under vacuum and dried at 50°-60° C. The obtained yields are about 20% of the starting racemic mixture.

I claim:

1. A process for the separation of folinic acids and the isolation of the calcium salt of the levorotatory folinic acid characterized by the steps of:
   a) treatment of racemic calcium folinate with the sodium salt of ethylendiaminotetraacetic acid, in the molar ratio of 0.5 moles of tetrasodium EDTA per each mole of racemic calcium folinate, and salting out of the resulting solution with sodium chloride;
   b) separation of the mother liquors from the resulting precipitate and treatment thereof with anhydrous calcium chloride with formation of a precipitate consisting of the desired product.

2. A process according to claim 1, characterized in that in said step (a) an aqueous solution of racemic calcium folinate is used and, further to tetrasodium EDTA, calcium chloride is added, also this in the ratio of 0.5 moles per mole of racemic calcium folinate.

3. A process according to claim 1, characterized in that the step (a) is effected at ambient temperature and under stirring.

4. A process according to claim 1, characterized in that the product obtained from the step (b) is subjected to purification through at least a crystallization.

5. A process according to claim 4, characterized in that said crystallization is effected by suspending the raw product in water, regulating the pH to 5.5, bringing to a 55°-60° C. temperature, adding sodium or calcium chloride in a quantity corresponding to a quarter of the weight on dry basis of the product and bringing the pH to 9.2, always maintaining the 55°-60° C. temperature and leaving to crystallize without any stirring.

* * * * *